United States Patent [19]

Crawford et al.

[11] Patent Number: 5,451,691

[45] Date of Patent: Sep. 19, 1995

[54] SYNTHESIS OF COSMETIC INGREDIENTS

[75] Inventors: Duncan J. Crawford, Southampton, United Kingdom; Anthony V. Rawlings, Wyckoff; Ian R. Scott, Allendale, both of N.J.

[73] Assignee: Elizabeth Arden, Co., Division of Conopco, Inc., New York, N.Y.

[21] Appl. No.: 335,215

[22] Filed: Nov. 7, 1994

Related U.S. Application Data

[63] Continuation of Ser. No. 57,730, May 5, 1993, abandoned.

[30] Foreign Application Priority Data

May 7, 1992 [GB] United Kingdom ................ 9209860

[51] Int. Cl.$^6$ ........................................... C07C 231/00
[52] U.S. Cl. ........................... 554/68; 554/37; 554/61; 554/63
[58] Field of Search ..................... 554/37, 52, 61, 63, 554/68, 69

[56] References Cited

U.S. PATENT DOCUMENTS 3,660,566  5/1972  Vincent et al. .................. 424/95

FOREIGN PATENT DOCUMENTS

| 0097059 | 12/1983 | European Pat. Off. |
| 0227994 | 7/1987 | European Pat. Off. |
| 0293006 | 11/1988 | European Pat. Off. |
| 0398272 | 11/1990 | European Pat. Off. |
| 0482860 | 4/1992 | European Pat. Off. |
| 2126892 | 4/1984 | United Kingdom |
| 2178312 | 2/1987 | United Kingdom |

OTHER PUBLICATIONS

PCT Search Report in a corresponding international Application No. PCT/GB93/00932, (Aug. 19, 1993).
Garner et al., "A Stereodivergent Synthesis of D-erythro-Sphingosine and D-threo-Sphingosine from L-Serine", Journal of Organic Chemistry, vol. 53, Issue 14-19, (1988), pp. 4395-4398.
Herald, Peter, "Synthesis of D-erythro- and D-threo-Sphingosine Derivatives from L-Serine", Helvetica Chimica ACTA—Vol. 71, (1988), pp. 354-362.
Abrams, Suzanne R., "A General Synthesis of Long Chain ω- and (ω-1)-Hydroxy Fatty Acids", Chemistry and Physics of Lipids, 28, (1981), pp. 379-384.
Great Britian Search Report in corresponding British Application No. 9209860.7, Jun. 30, 1992.

Primary Examiner—José G. Dees
Assistant Examiner—Deborah D. Carr
Attorney, Agent, or Firm—Rimma Mitelman

[57] ABSTRACT

A method of synthesis of ω-hydroxy fatty acid containing ceramides having the general structure (1).

$$Y-O-(C_aH_b)-\overset{O}{\overset{\|}{C}}-NH \atop \underset{CH_3-(CH_2)_n-A-CHOH}{|}CH-CH_2OH \quad (1)$$

where A represents $CH_2$ or $-CH=CH-$ Y represents a residue of a $C_{14}$ to $C_{22}$ fatty acid having the structure (2)

$$-\overset{O}{\overset{\|}{C}}-(C_xH_yZ_z)CH_3 \quad (2)$$

where
Z is —OH or an epoxy oxygen
x is an integer of from 12 to 20
y is an integer of from 20 to 40
z is 0 or an integer of from 1 to 4
a is an integer of from 8 to 50
b is an integer of from 10 to 100
and n is an integer of from 7 to 27.

7 Claims, No Drawings

SYNTHESIS OF COSMETIC INGREDIENTS

This is a continuation application of Ser. No. 08/057,730, filed May 5, 1993, now abandoned.

FIELD OF THE INVENTION

The invention relates to a method of synthesis of ω-hydroxy fatty acid containing ceramides.

BACKGROUND AND PRIOR ART

It is well established that ceramides have a vital role in the production and maintenance of the water permeability barrier of the skin. Ceramides, or substances closely related to them, have been widely disclosed as components of skin care compositions.

In particular EP 0 097 059 (Unilever) discloses the vital role played by ω-linoleoyl ceramides in the water barrier of the skin and describes the application for skin care of such ω-linoleoyl ceramides.

It is known in the art that skin ceramides (including ω-hydroxy fatty acid containing ceramides) may be extracted from mammalian stratum corneum cells.

It has been proposed for example in U.S. Pat. No. 3,660,566 (Lever Brothers Company), to extract animal stratum corneum from epidermis and then separate the stratum corneum into a lipid-rich fraction and a cellular fraction, and then to employ the lipid-rich fraction in cosmetic compositions.

It is also proposed in GB 2 178 312 (Kao Corporation) to extract lipids from horny cells of mammals such as the pig, and then to employ the lipid so extracted in cosmetic compositions which are useful for treating dry skin conditions in man.

However, to extract ω-hydroxy fatty acid containing ceramides in high enough levels for incorporation into skin care products causes problems. Furthermore it is undesirable for the source of the cosmetic ingredient to be from animals.

Synthetic Pseudo-ceramides have also been widely disclosed in the literature, for example by Kao Corporation in EP 0 227 994 which discloses synthetic analogues of ceramides which have some similar properties to natural ceramides but which are relatively cheaper to produce. However, the degree of skin benefit attributable to such analogues is limited to the extent that they do not fully mimic the natural ceramides of the skin.

It is therefore desirable to be able to synthesise naturally-occurring ω-hydroxy fatty acid containing ceramides using a synthesis route, which is not too expensive, to allow the possibility of the synthesised ceramides being incorporated at functional levels into cosmetic compositions.

DEFINITION OF THE INVENTION

Accordingly, the invention provides:

A method of synthesising an ω-hydroxy fatty acid containing ceramide having the general structure (1):

$$Y-O-(C_aH_b)-\overset{O}{\underset{\|}{C}}-NH \atop |\atop CH-CH_2OH \atop |\atop CH_3-(CH_2)_n-A-CHOH \quad (1)$$

where
A represents $CH_2$ or $-CH=CH-$

Y represents a residue of a $C_{14}$ to $C_{22}$ fatty acid having the structure (2)

$$-\overset{O}{\underset{\|}{C}}-(C_xH_yZ_z)CH_3 \quad (2)$$

where
Z is $-OH$ or an epoxy oxygen
x is an integer of from 12 to 20
y is an integer of from 20 to 40
z is 0 or an integer of from 1 to 4
a is an integer of from 8 to 50
b is an integer of from 10 to 100
and n is an integer of from 7 to 27 selected from synthesis A, synthesis B, synthesis C and synthesis D wherein;

synthesis A comprises;

(ia) coupling an ω-hydroxy fatty acid with a protected carboxyl group having the general structure (3);

$$HO(C_aH_b)COOP \quad (3)$$

where P is a protection group with a $C_{14-22}$ fatty acid having the general structure (4);

$$OH-\overset{O}{\underset{\|}{C}}-(C_xH_yZ_z)CH_3 \quad (4)$$

to give an intermediate having the general structure (5);

$$CH_3(C_xH_yZ_z)-\overset{O}{\underset{\|}{C}}-O-(C_aH_b)-COOP \quad (5)$$

(iia) deprotection of the intermediate (5) to provide an intermediate having the general structure (6);

$$CH_3(C_xH_yZ_z)-\overset{O}{\underset{\|}{C}}-O-(C_aH_b)-COOH \quad (6)$$

and
(iiia) coupling the intermediate (6) with sphingosine having the general structure (7);

$$NH_2 \atop |\atop CH-CH_2OH \atop |\atop CH_3(CH_2)_n-A-CHOH \quad (7)$$

to form the ω-hydroxy fatty acid containing ceramide having the general structure (1);

synthesis B comprises;

(ib) converting a terminal acetylenic alcohol having the general structure (8);

$$HC\equiv CCH_2(C_aH_b)CH_2OH \quad (8)$$

into an intermediate having the general structure (9);

$$HC\equiv CCH_2(C_aH_b)COOP \quad (9)$$

then converting this intermediate into an intermediate having the general structure (10);

$$HOCH_2(C_aH_b)COOP \quad (10)$$

(iib) coupling the intermediate (10) with a $C_{14-22}$ fatty acid having the general structure (4);

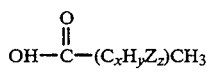 (4)

to give an intermediate having the general structure (11);

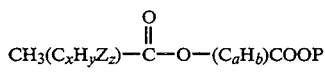 (11)

then selectively converting the intermediate (11) into an intermediate having the general structure (6);

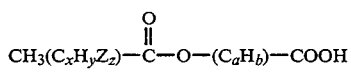 (6)

and
(iiib) coupling the intermediate (6) with sphingosine having the general structure (7);

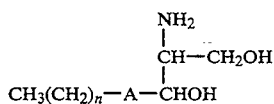 (7)

to form the ω-hydroxy fatty acid containing ceramide having the general structure (1);
synthesis C comprises:
(ic) coupling an ω-hydroxy fatty acid having the general structure (12);

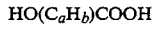 (12)

with a sphingosine having the general structure (7);

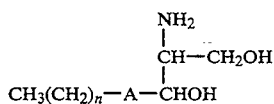 (7)

to form an intermediate having the general structure (13);

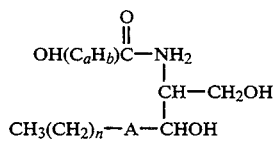 (13)

(iic) protection of the hydroxyl groups of the intermediate having the general structure (13) to give an intermediate having the general structure (14);

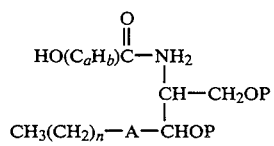 (14)

(iiic) esterification of the intermediate (14) with a $C_{14}$ to $C_{22}$ fatty acid having the general structure (4);

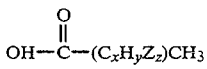 (4)

and
(ivc) removal of the protection groups to provide the ω-hydroxy fatty acid containing ceramide having the general structure (1); and
synthesis D comprises:
(id) coupling a long chain diol having the general structure (15);

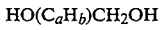 (15)

with a $C_{14-22}$ fatty acid having the general structure (4);

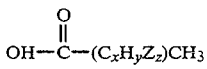 (4)

to give an intermediate having the general structure (16);

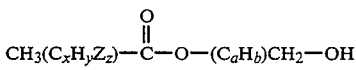 (16)

(iid) oxidation of the free hydroxyl group on intermediate (16) to give an intermediate having the general structure (6);

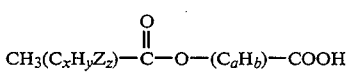 (6)

and
(iiid) coupling the intermediate (6) with sphingosine having the general structure (7);

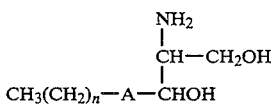 (7)

to form the ω-hydroxy fatty acid containing ceramide having the general structure (1).

DISCLOSURE OF THE INVENTION

The invention concerns the synthesis of ω-hydroxy fatty acid containing ceramides having the general structure (1) given above.

With reference to structure (1) the value of a is preferably an integer of from 20 to 30 and the value of b is most preferably an integer of from 40 to 60.

Also with reference to structure (1) the group Y preferably represents a straight chain saturated $C_{14-18}$ fatty acid residue or a straight chain all cis n-6,9 di-unsaturated $C_{16-18}$ fatty acid residue, more preferably represents a fatty acid selected from oleic acid, palmitic acid, stearic acid and linoleic acid, and is most preferably a linoleic acid residue.

Also with reference to structures (1) or (7), n is preferably 12.

Also with reference to structures (1) or (7), A is preferably the group —CH=CH—.

With reference to synthesis A, B and C, the protection group (P) is preferably t-butylalcohol.

Important in the synthesis of the ceramides having the general structure (1) is the order in which the component parts (sphingosine, ω-hydroxy fatty acid and C$_{14-22}$ fatty acid) are coupled together. There are four alternative synthesis routes (is synthesis A, B, C and D).

Synthesis A comprises;

(ia) coupling a ω-hydroxy fatty acid with a protected carboxyl group having the general structure (3);

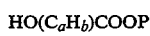  (3)

where P is a protection group with a C$_{14-22}$ fatty acid having the general structure (4);

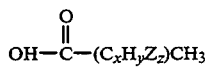  (4)

under standard esterification reaction conditions, for example dicyclohexylcarbodiimide (DCC)/dimethylamino pyridine (DMAP), to give any intermediate having the general structure (5);

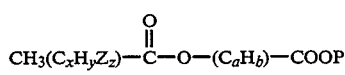  (5)

(iia) deprotection of the intermediate (5), preferably by treatment with toluenesulphonic acid in refluxing benzene to provide an intermediate having the general structure (6);

  (6)

and (iiia) coupling the intermediate (6) with sphingosine having the general structure (7);

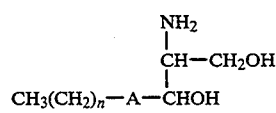  (7)

under standard peptide bond coupling conditions (for example, DCC/DMAP in chloroform, 2 hours, 0° C.) to form the ω-hydroxy fatty acid containing ceramide having the general structure (1).

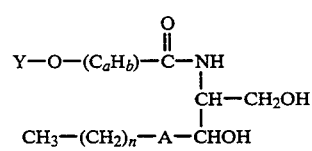  (1)

Synthesis B comprises;

(ib) converting a terminal acetylenic alcohol having the general structure (8);

  (8)

into an intermediate having the general structure (9);

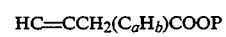  (9)

then converting this intermediate into an intermediate having the general structure (10);

  (10)

(iib) coupling the intermediate (10) with a C$_{14-22}$ fatty acid having the general structure (4);

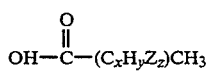  (4)

to give an intermediate having the general structure (11);

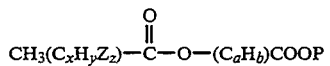  (11)

then selectively converting the intermediate (11) into an intermediate having the general structure (6);

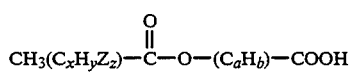  (6)

and (iiib) coupling the intermediate (6) with sphingosine having the general structure (7);

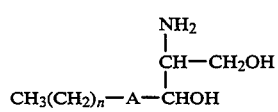  (7)

under standard peptide bond coupling conditions (for example, DCC/DMAP in chloroform, 2 hours, 0° C.) to form the ω-hydroxy fatty acid containing ceramide having the general structure (1).

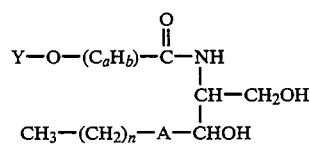  (1)

Synthesis C comprises;

(ic) coupling an ω-hydroxy fatty acid having the general structure (12);

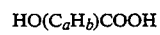  (12)

with a sphingosine having the general structure (7);

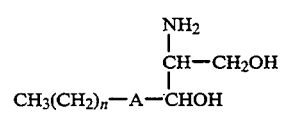  (7)

to form an intermediate having the general structure (13);

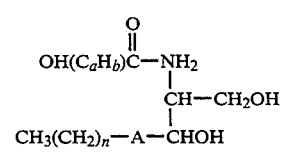  (13)

(iic) protection of the hydroxyl groups of the intermediate having the general structure (13) to give an intermediate having the general structure (14);

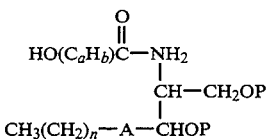
(14)

(iiic) esterification of the intermediate (14) with a $C_{14}$ to $C_{22}$ fatty acid having the general structure (4):

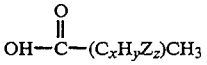
(4)

and (ivc) removal of the protection groups to provide the ω-hydroxy fatty acid containing ceramide having the general structure (1).

Synthesis D comprises:

(id) coupling a long chain diol having the general structure (15):

$HO(C_aH_b)OH$ (15)

with a $C_{14-22}$ fatty acid having the general structure (4);

(4)

to give an intermediate having the general structure (16);

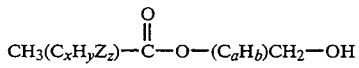
(16)

(iid) oxidation of the free hydroxyl group on intermediate (16) to give an intermediate having the general structure (6);

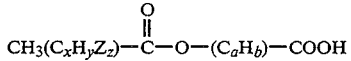
(6)

and (iiid) coupling the intermediate (6) with sphingosine having the general structure (7);

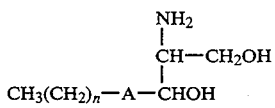
(7)

under standard peptide bond coupling conditions (for example DCC/DMAP in chloroform, 2 hours, 0° C.) to form the ω-hydroxy fatty acid containing ceramide having the general structure (1).

Synthesis routes A and D are preferred.

Specific examples of these synthesised ceramides are those having the structures (17) to (21):

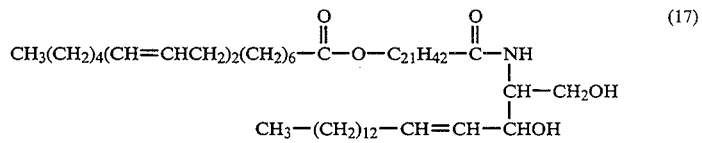
(17)

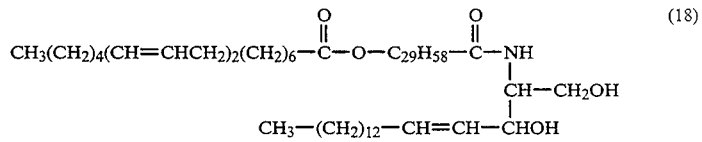
(18)

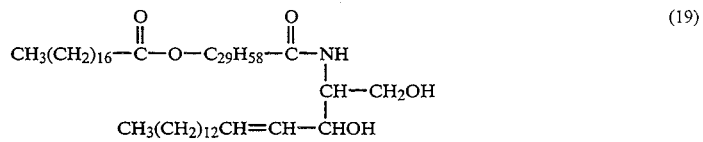
(19)

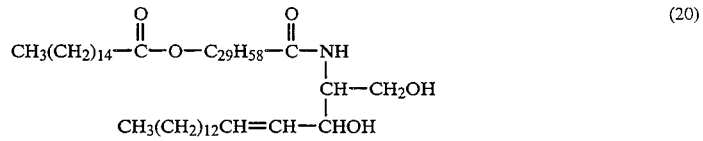
(20)

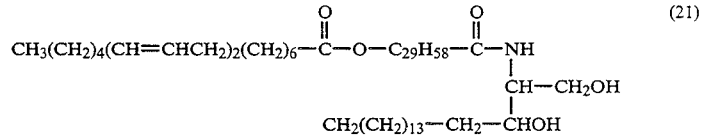
(21)

The ω-hydroxy fatty acid

The ω-hydroxy fatty acid having the general structure (12);

(12)

may be obtained either by synthesis or by extraction from a natural source.

Any appropriate synthesis route for ω-hydroxy fatty acids may be used. An example of a suitable synthesis route is disclosed by Abrams (1981) in Chemistry and Physics of Lipids 2B, 379 which describes the synthesis of ω-hydroxydocosanoic acid.

The synthesis of ω-hydroxy fatty acids is based upon the "acetylenic zipper" reaction in which potassium or sodium aminopropylamine effects the isomerization of an internal triple bond of an alkyne or alkyn-1-ol exclusively to the terminal alkyne. Jones oxidation, esterification, hydroboration and oxidation yielded the ω-hydroxy fatty acid and/or ester.

ω-hydroxy fatty acids may be isolated from plants, beeswax, or woolwax.

The required ω-hydroxy fatty acid is preferably synthesised.

Sphingosine

Synthesis of sphingosine has been disclosed by Garner et al (1988) J Org Chem 53 4396; Garner et al (1987) J Org Chem 52 2361 and Herald et al (1988) Helvetica Chimioa Acta 71 354.

Sphingosine was shown to be synthesised from either commercially available N-BOC-serine or from L-serine which had been treated with di-tart-butyl dicarbonate followed by esterification with diazomethane. The oxazolidine was formed under acid-catalysed conditions and the free aldehyde was reacted with lithium-1-pentadecyne to derive propargylic alcohols which were reduced to sphingosine.

However, the following novel synthesis route shown in Scheme 1 is preferred to any previously disclosed synthesis route.

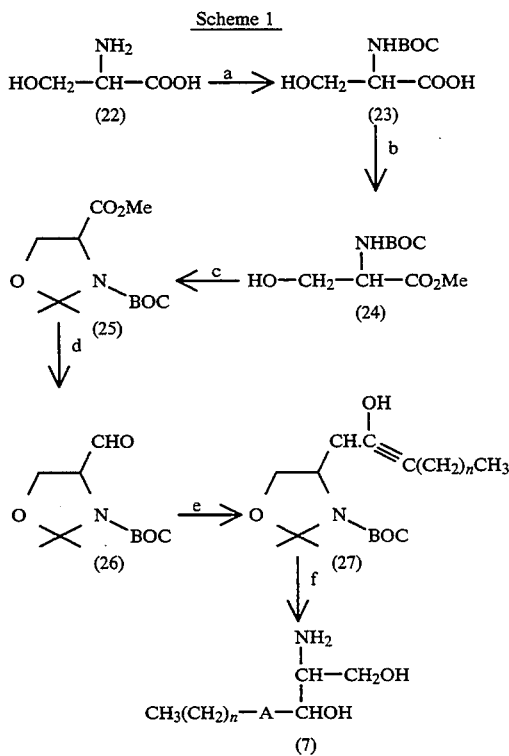

Scheme 1

Reagents
a (BOC)$_2$O, aqueous NaOH
b CH$_2$N$_2$, ether

-continued
Scheme 1
c Dimethoxypropane, TsOH, benzene
d Di-iso-butylaluminum hydride, toluene
e CH$_3$(CH$_2$)$_n$C≡CLi, tetrahydrofuran,
   Hexamethylphosphorus-triamide (HMPT)
f Lithium, ethylamine In order to obtain the molecule with the correct stereochemistry, the cheap and readily available L-serine (22) was used as a starting material, effectively establishing the correct configuration for position 2 on the sphingosine chain. In the reaction sequence the amino group of serine was first protected with the tert-butoxycarbonyl (BOC) group (23), which is converted to the methyl ester (24) on treatment with ethereal diazomethane. The remaining NH and OH groups on this molecule are then protected by conversion to the cyclic oxazolidine (25) on treatment with dimethoxypropane with a catalytic amount of toluene sulphonic acid in benzene, and the ester function reduced to the aldehyde (26) on treatment with di-iso-butylaluminium hydride (DI-BAL) in toluene. Treatment of this aldehyde with CH$_3$(CH$_2$)$_n$C≡CLi in tetrahydrofuran (THF) in the presence of Hexamethylphosphorustriamide (HMPT) gave a mixture of erythro (27), and threo diastereoisomers. The erythro diastereoisomer (27) with the correct stereochemistry for D-erythro-sphingosine was obtained following chromatography on silica gel. Treatment of (27) with lithium in ethylamine gave the target molecule D-erythro-sphingosine (7).

Note that by using different conditions it is possible to almost completely reverse the stereoselection in the addition of the lithium acetylide to the aldehyde (26). Thus this synthesis can be easily modified to produce any of the four stereoisomers of sphingosine with any given chain length. The naturally occurring D-erythro-stereoisomer is preferred.

Use Of Synthesised Ceramides (1) In Cosmetic Compositions

Ceramides synthesised in accordance with the invention can be incorporated into cosmetic compositions intended for topical application to human skin, hair, or nails in an amount of from 0.0001 to 10%, preferably from 0.001 to 5% by weight of such compositions.

Topical application to human skin, hair or nails of such cosmetic compositions can improve the barrier and elasticity properties of the epidermis of the skin, thus improving moisture retention and as a treatment of dry skin or detergent damaged skin.

EXAMPLES

The invention is illustrated by the following examples.

EXAMPLE 1

Synthesis of C$_{22}$ lineoyl ceramide 1 (17)

Synthesis of ω-hydroxy acid and coupling with linoleic acid to form 22-linoleoyloxydocosanic Acid (42)

The C$_{22}$ chain was put together as follows: (see Scheme 2) commercially available 11-bromoundecanol (28) was protected as the THP ether by treatment with dihydropyran in the presence of toluenesulphonic acid to give the compound (29) in 99% yield. Alkylation of this material with 1-Lithioundecyne in dimethoxyethane gave the product with C$_{22}$ chain length (30) in 80% yield as a crystalline solid. This material was converted to the terminal acetylenic alcohol (31) on treatment with strongly basic conditions (acetylene zip reaction). This material is extremely significant in our synthetic route as it contains the $C_{22}$ chain length and has functionality which can be easily manipulated at both ends. Conversion of (31) to the corresponding acetylenic acid (32) was achieved in 83% yield by the use of Jones reagent, and (32) was in turn converted to the tert-butyl ester (33) in 86% yield on treatment with Dicyclohexyl carbodimide (DCC), Dimethylamino pyridine (DMAP); Dimethylamino pyridine trifluoro acetic acid (DMAP.TFA) and tert-butyl alcohol in chloroform. The acetylenic function on (33) was converted to the required alcohol (34) on treatment with borane di-methyl sulphide complex followed by alkaline oxidation, thus giving the initial target of ω-hydroxydocosanic acid (34) with selective protection on the acid functionality. As expected, this compound was found to couple smoothly with linoleia acid under standard conditions (DCC/DMAP) to give the linoleic acid-ω-hydroxydocosanic acid fragment of ceramide protected as the tert-butyl ester (35). Deprotection of this material occurred smoothly in 73% yield on treatment with toluenesulphonic acid in refluxing benzene to give the required linoleic acid-ω-hydroxydocosanic acid fragment (42) as a white crystalline solid in good overall yield (15% from 11-bromoundecanol).

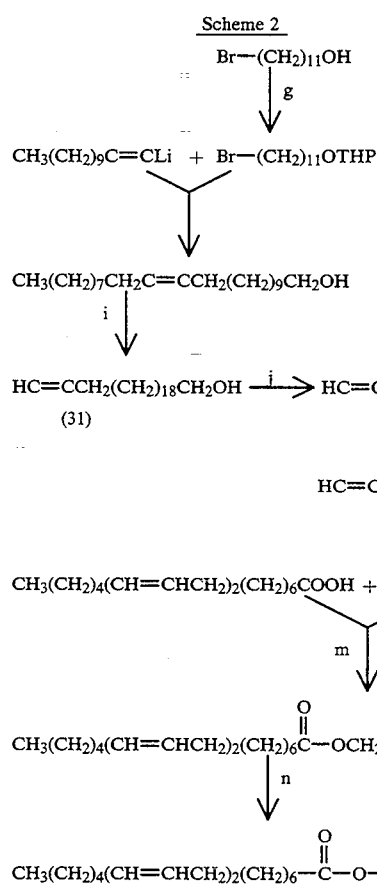

Reagents g dihydropyran, toluene sulponic acid hydrate ($T_6OH$), $CH_2Cl_2$
h Lithium amide, dimethoxyethane
i NaH, Diaminopropane
j Jones reagent, acetone -continued
Scheme 2 k DCC, DMAP, DMAP.TFA, tertiary butyl alcohol, $CHCl_3$
l Borane dimethyl sulphide complex, THF
m DCC, DMAP, $CHCl_3$
n TaOH, Benzene Experimental For The Synthesis Of $C_{22}$ Linoleic Ceramide 1

11-Bromoundecanol THP ether (29)

A solution containing 11-bromoundecanol (50 g, 0.199 mol) and dihydropyran (20 ml, 18.44 g, 0.219 mol) in dry, ethanol-free methylene chloride (333 ml) at room temperature under an atmosphere of nitrogen was treated with a catalytic amount of toluenesulphonic acid, and the resulting solution stirred for 10 minutes, after which time tlc indicated the reaction to be complete. Aqueous sodium bicarbonate was added, the organic layer separated, dried ($MgSO_4$), filtered and evaporated. The crude material obtained in this manner was purified by chromatography on silica (500 g). Elution with petrol followed by 1% ether/petrol gave the title compound (29) as a clear oil (66.19 g, 99%).

Docos-12-ynol (30)

A solution of undec-1-yne (15.22 g, 0.1 mol) in dimethoxyethane (100 ml) at room temperature under nitrogen was treated with lithium amide (2.30 g, 0.1 mol) and the resulting solution heated at reflux for 4 hour, after which time a solution of 11-bromoundecanol THP ether (29) in DME (50 ml) was added and reflux maintained over night, after which time tlc indicated the reaction to be complete. The mixture was poured onto water and extracted with ether three times. The combined organics were dried ($MgSO_4$), filtered and evaporated to leave a red oil (approx 60 g) which was dissolved in methanol (300 ml), treated with a catalytic amount of toluene sulphonic acid and heated at reflux for 30 minutes. On cooling, flesh coloured crystals separated which were collected and washed with methanol to give docos-12-ynol (30) (23.61 g, 80%) mp 38°–39° C.

Docos-21-ynol (31)

Diaminopropane (DAP) (150 ml) at room temperature under nitrogen was stirred and treated with sodium hydride (100%, 13.55 g, 0.56 mol). The resulting solution was then warmed to 70° C. for 1 hour after which time further DAP (30 ml) is added followed by docos-12-ynol (22 g, 0.068 mol). The resulting solution was then left at 70° C. overnight, cooled and poured into water. The aqueous mixture was extracted three times with chloroform, the combined organic dried ($MgSO_4$), filtered and evaporated to leave a pinkish residue. Recrystallisation from methanol gave docos-21-ynol (31) (18.05 g, 84%) as white crystals mp 64°–70° C.

Docos-21-ynoic Acid (32)

Docos-21-ynol (12 g, 0.037 mol) was dissolved in warm acetone (600 ml) treated with Jones reagent (20 ml). After stirring for 30 minutes tlc showed complete reaction so the excess Jones reagent was quenched with propane-2-ol and the volatile components removed in vacuo. The organic fractions were combined, dried ($MgSO_4$), filtered and evaporated to leave docos-21-ynoic acid (32) as a pale green solid (10.4 g, 83%).

Docos-21-ynoic Acid. Tert.-Butyl Ester (33)

The acid (32) (6.4 g, 0.019 mol) was dissolved in dry, ethanol free, chloroform (120 ml) at room temperature under nitrogen and sequentially treated with dimethylaminopyridine (2.55 g, 0.0209 mol), tert butanol (14.09 g, 0.19 mol), dimethylaminopyridine-trifluoroacetic acid complex (4.94 g, 0.0209 mol) and dicyclohexylcarbodiimide (4.31 g, 0.0209 mol). The resulting solution was stirred at room temperature overnight then filtered, the organic layer washed with 5% acetic acid in water, then dried (MgSO$_4$), filtered and evaporated. The residue was purified by chromatography on silica gel (50 g). Elution with 10% ether in petrol gave the title compound (33) as white crystals (6.45 g, 86%) mp 44°–45° C.

Tert.-Butyl 22-Hydroxydocosanoate (34)

A solution of the acetylene (33) (0.4 g, 1.02 mmol) in dry THF (5 ml) at room temperature under nitrogen was treated with borane-dimethyl sulphide complex (1.04 ml of a 2M solution in THF, 2.08 mmol) and the resulting solution stirred for 1 hour, after which time no starting material was present on tlc. The reaction was then treated sequentially with water (2 ml), 2N aqueous sodium hydroxide (1 ml) and 30% hydrogen peroxide (1 ml). The resulting solution was left a further 15 minutes, then ethyl acetate added and the organic layer separated. The aqueous layer was re-extracted with ethyl acetate, the organic layers combined, dried (MgSO$_4$) and evaporated. The crude product obtained in this manner was purified on silica (5 g). Elution with 10% ethyl acetate in petrol gave tert.-butyl 22-hydroxydocosanoate (34) as a white solid (0.23 g, 54%).

22-Linoleoyloxydocosanoic Acid, Tert.-Butyl Ester (35)

A solution containing tert.-butyl 22-hydroxydocosanoate (34) (2.17 g, 5.26 mmol) and linoleic acid (1.45 g, 5.26 mmol) in dry ethanol free chloroform (50 ml) at room temperature under nitrogen was treated with dimethylaminopyridine (0.064 g, 0.524 mmol) and dicyclohexylcarbodiimide (1.19 g, 5.78 mmol), and the resulting solution was stirred for three hours at room temperature, after which time tlc indicated that the reaction is complete. The mixture was filtered and the filtrate washed with 5% acetic acid, then water, then dried (MgSO$_4$), filtered and evaporated. The residue was purified by chromatography on silica (30 g). Elution with petrol followed by 5% ether in petrol gave the title compound (35) as a white wax (2.18 g, 79%).

22-Linoleoyloxydocosanic Acid (42)

A solution of the ester (35) (0.15 g, 0.222 mmol) in dry benzene (3 ml) under nitrogen was treated with a catalytic amount of toluenesuphonic acid and the resulting solution heated at reflux for 5 hours, after which time no starting material remained on tlc. The volatile components were removed in vacuo and the residue chromatographed on silica (5 g). Elution with 10% ether in petrol gave the title compound (42) as a white wax (0.1 g, 73%).

N-Boc-L-Serine (23)

L-Serine (10 g, 0.95 mol) was dissolved in 1N sodium hydroxide (195 ml) and the solution stirred and cooled to 0° C. A solution of BOC anhydride (24.7 g, 0.113 mol) in dioxane (88 ml) was then added and the resulting solution allowed to stir up to room temperature over 1.5 hours, after which time tlc showed the reaction to be complete. The solution was then reduced to half volume in vacuo and the pH adjusted to 3 by the addition of 1N potassium bisulphate (195 ml). The mixture was then extracted with ethyl acetate twice, the organic combined, dried (MgSO$_4$), filtered and evaporated to leave the product (23) as a sticky foam (18.54 g, 96%).

N-Boc-L-Serine Methyl Ester (24)

A solution of the acid (23) in ether (200 ml) at room temperature was treated with ethereal diazomethane until the yellow colour just persisted and tlc showed there to be no starting material present. The volatiles were then removed in vacuo leaving the product (24) as a light orange oil (17.89 g, 90%).

3-(1,1-Dimethylethyl)4-Methyl(S)-2,2-Dimethyl-3,4-Oxazolidiedincarboxylate (25)

A solution of N-Boc-L-serine ester (24) (17.89 g, 0.0816 mol) in benzene (285 ml) was treated with dimethoxypropane (21 ml, 0.17 mol) and toluenesulphonic acid (0.2 g, catalytic). The resulting solution was then heated at reflux under an atmosphere of nitrogen for 30 minutes, and the volatile components removed under reduced pressure. The residue was dissolved in ether, washed with aqueous sodium bicarbonate, dried (MgSO$_4$) filtered and evaporated. The residue was then distilled at reduced pressure to give the title compound (25) as a clear oil (17.24 g, 81%) bp 94°–98° C.

1,1-Dimethylethyl(S)-4-Formyl-2,2-Dimethyl-3-Oxazolidinecarboxylate (26)

The ester (25) (27.70 g, 0.106 mol) was dissolved in dry toluene (206 ml) under an atmosphere of nitrogen and cooled to −78° C. with stirring. A solution of DIBAL (120 ml of a 1.5M solution in toluene, 0.18 mol) was added over a 1 hour period with care being taken to prevent the internal temperature to rise above −65° C. The reaction was then allowed to stir for a further 2 hours at −78° C., then quenched with cold (−78° C.) methanol and the resulting solution poured into ice cold 1N HCl. Ethyl acetate (500 ml) was then added and the solid aluminum salts removed by filtration. The filtrate was extracted twice with ethyl acetate, and the organic layers combined, dried (MgSO$_4$), filtered and evaporated. The residue was then distilled at reduced pressure to give the title compound (26) as a colourless oil (16.65 g, 68%) bp 102–104° C.

1,1-Dimethylethyl (R-(R*,S*)1-2,2-Dimethyl-4-(-Hydroxy-2-Hexadecynyl)-3-Oxazolidinecarboxylate (27)

(where in structure 27 n is 12)

A solution of pentadec-1-yns (5 g, 0.024 mol) in dry THF (130 ml) was cooled to −20° C. under nitrogen, and treated with a solution of buytllithium (13.75 ml of a 1.6 m solution in THF, 0.022 mol) over ten minutes. The resulting solution was maintained at −20° C. for two hours and then treated with freshly distilled HMPT (6.44 ml) followed by a solution of the aldehyde (26) (4.23 g, 0.818 mol) in THF (10 ml). The resulting solution was then allowed to warm to room temperature over two hours, quenched with ammonium chloride solution and extracted three times with ether. The combined ethereal layers were evaporated to dryness and the residue purified by chromatography on silica (50 g).

Elution with 10% ethyl acetate in petrol gave the title compound (27) as a clear oil (4.24 g, 52%).

D-Erythro-Sphingosine (7)

(where in structure 7, n is 12 and A is the group —CH=CH—)

Ethylamine (300 ml) under nitrogen was cooled to −78° C. with stirring and treated with lithium metal (2.25 g, 0.324 mol) and the resulting blue colour allowed to develop over 30 minutes at this temperature. A solution of the acetylene (27) (10.04 g, 0.229 mol) in THF (300 ml) was cooled to −20° C. and added over a ten minute period and the resulting solution maintained for 1 hour at −78° C. and allowed to warm to room temperature overnight. Solid ammonium chloride (38.65 g, 0.729 mol) was then added (fizzing) and the volatiles removed in vacuo. The residue was partitioned between ether and water, the organic layer separated, washed with water, dried (MgSO4), filtered and evaporated to leave D-erythro-sphingosine as an off-white solid (6.36 g, 92%).

$C_{22}$ lineoyl ceramide 1 (17)

A solution containing the acid (42) and sphingosine (7) in methylene chloride at room temperature was treated with chloromethylpyridinium iodide and triethylamine. The resulting solution was stirred for one hour, then diluted with methylene chloride and washed with water three times, then dried, filtered and evaporated to leave $C_{22}$-lineoyl ceramide 1 (17).

CHARACTERISATION

Infra-Red Spectroscopy

The sample of $C_{22}$ lineoyl ceramide 1 (17) was run as a cast film from CHCl3 onto a KBr plate, on a Bruker IFS-88 FTIR spectrometer. The following features are fully consistent with the proposed structure for Ceramide 1.

| | |
|---|---|
| alkyl-H | 3000 − 2800 cm − 1 |
| OH | 3292 cm − 1 |
| Ester C=O | 1738 cm − 1 |
| Amide C=O | −1643 cm − 1 |
| C=C | −1643 cm − 1 |
| Amide N—H | 1556 cm − 1 |

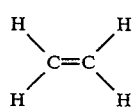

3011 cm − 1

EXAMPLE 2

Synthesis of $C_{30}$ Lineolyl Ceramide 1 (18)

Synthesis of $C_{30}$ Linoleic Ceramide

The $C_{30}$ linoleoyl ceramide is the major component of ceramide one in human stratum corneum.

The $C_{30}$ ω-hydroxy fatty acid was synthesised from octadiyne and 11-bromoundecanol prior to synthesis of the 30-linoleoyloxytriacontanol by esterification with linoleoyl chloride. The acid is formed by oxidation with chromic acid before coupling to sphingosine with chloromethylpyridinium iodide. Like the $C_{22}$ species, the major contaminant of the reaction product was the acyl acid. However, the chemistry presented here was more efficient giving a 80% purity. Ceramide one was purified by chromatography on aminopropyl bonded silica.

Scheme 3

(Octadiyne) (36) →$^o$ (37) with ≡(CH2)11OH and ≡(CH2)11OH

↓ p

HOCH2(CH2)28CH2OH (38)

CH3(CH2)4(CH=CHCH2)2(CH2)6COCl (39)

↓ q

CH3(CH2)4(CH=CHCH2)2(CH2)6CO2CH2(CH2)28CH2OH (40)

↓ r

CH3(CH2)4(CH=CHCH2)2(CH2)6CO2CH2(CH2)27CH2CO2H (41)

(7) ↓ s

CH3(CH2)4(CH=CHCH2)2(CH2)6CO2CH2(CH2)26CO2NH—CH—CH2OH (18)
 |
 CH3(CH2)12CH=CH—CHOH

Reagents
o Butyllithium, HMPA, 11-bromoundecanol, tetrahydrofuran (THF) then TsOH, Meoh
p H2, Pd, THF
q Pyridine, CHCl3
r Chromic acid, ether
s Chloromethylpyridinium iodide, triethylamine, CH2Cl2

Experimental for the Synthesis of $C_{30}$ Linoleic Ceramide 1

1,30-Dihydroxytriaconta-12,18-Diyne (37)

A solution of octadiyne (9.3 ml; 0.07 mol) in dry THF (200 ml) at 0° C. under nitrogen was treated with HMPA (24.38 ml, 0.14 mol) and n-butyllithium (87.61 ml of a 1.6M solution in hexane; 0.14 mol). The resulting solution was left for ten minutes at 0° C. and then treated with a solution of 11-bromoundecanol (47 g, 0.14 mol). The resulting solution was allowed to stir at room temperature for four hours and then heated at reflux overnight, cooled, diluted with water and extracted with ether. The organic layer was washed with water twice, then dried, evaporated and the residue dissolved in methanol (60 ml). This solution was treated with a catalytic amount of toluenesulphonic acid and heated at reflux for ten minutes. On cooling the title compound (37) separated as pale yellow crystals (18.42 g, 59%).

1,30-Triacontadiol (38)

A solution of 1,30-dihydroxytriaconta-12,18-diyne (11 g, 0.024 mol) in the THF (440 ml) was maintained at room temperature under nitrogen and treated with 10% lead on charcoal (1.1 g). An atmosphere of hydrogen was introduced and the flask external temperature raised to 60° C. The reaction was allowed to proceed overnight, then filtered through celite and allowed to cool, which caused the product to separate as white crystals (10.67 g, 95%).

30-Linoleoyloxytriacontanol (40)

1,30-Triacontadiol (38) (2.5 g, 5.5 mmol) was dissolved in dry, ethanol free chloroform at 60° C. under nitrogen and treated with pyridine (0.49 ml; 6.05 mmol). The resulting solution was treated with a solution of linoleoyl chloride (39) (1.64 g; 5.5 mmol) in chloroform (20 ml) over a twenty minute period and then maintained at 60° C. for a further thirty minutes, then cooled, diluted with chloroform, washed with water three times, dried, filtered and evaporated. The crude product obtained in this manner was purified on silica (30 g). Elution with chloroform gives the title compound (40) as a white solid (1.73 g; 44%).

30-Linoleoyloxytriacontanoic Acid (41)

The alcohol (40) (1.73 g, 2.41 mmol) was dissolved in ether (200 ml) at 30° C. and treated with chromic acid (4 ml of a 0.67M solution; 2.68 mmol). The resulting solution was allowed to stir and cool to room temperature over two hours during which time two further 1 ml portions of chromic acid were added. Propan-2-ol (5 ml) was then added and the ethereal solution washed with water four times, then dried, filtered and evaporated to leave the title compound (41) as a white powder (1.57 g; 89%).

$C_{30}$-Linoleic Ceramide (18)

A solution containing the acid (41) (1.57 g, 2.15 mmol) and sphingosine (0.643 g, 2.15 mmol) in methylene chloride (175 ml) at room temperature was treated with chloromethylpyridinium iodide, (0.548 g, 2.15 mmol) and triethylamine (0.6 ml; 4.3 mmol). The resulting solution was stirred for one hour, then diluted with methylene chloride (200 ml) and washed with water three times, then dried, filtered and evaporated to leave $C_{30}$-linoleic ceramide (18) as a light-brown wax (2.17 g, 98%).

We claim:

1. A method of synthesising an ω-hydroxy fatty acid containing ceramide having the general structure (1)

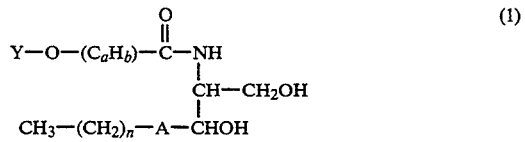

where

A represents $CH_2$ or $-CH=CH-$

Y represents a residue of a $C_{14}$ to $C_{22}$ fatty acid having the structure (2)

where

Z is —OH or an epoxy oxygen x is an integer of from 12 to 20 y is an integer of from 20 to 40 z is 0 or an integer of from 1 to 4 a is an integer of from 8 to 50 b is an integer of from 10 to 100 and n is an integer of from 7 to 27 selected from synthesis A, synthesis B, synthesis C and synthesis D wherein;

synthesis A comprises;

(ia) coupling an ω-hydroxy fatty acid with a protected carboxyl group having the general structure (3)

where P is a protection group with a $C_{14-22}$ fatty acid having the general structure (4);

to give an intermediate having the general structure (5);

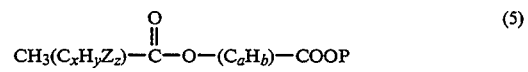

(iia) deprotection of the intermediate (5) to provide an intermediate having the general structure (6);

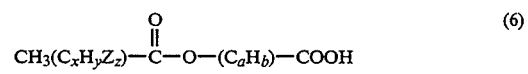

and (iiia) coupling the intermediate (6) with sphingosine having the general structure (7);

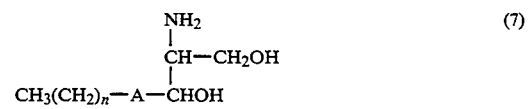

to form the ω-hydroxy fatty acid containing ceramide having the general structure (1);
synthesis B comprises;
(ib) converting a terminal acetylenic alcohol having the general structure (8);

into an intermediate having the general structure (9);

then converting this intermediate into an intermediate having the general structure (10);

(iib) coupling the intermediate (10) with a $C_{14-22}$ fatty acid having the general structure (4);

to give an intermediate having the general structure (11);

then selectively converting the intermediate (11) into an intermediate having the general structure (6);

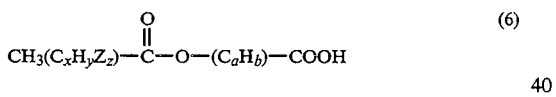

and
(iiib) coupling the intermediate (6) with sphingosine having the general structure (7);

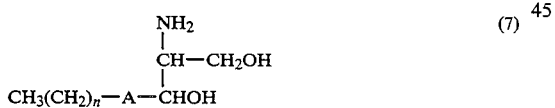

to form the ω-hydroxy fatty acid containing ceramide having the general structure (1);
synthesis C comprises:
(ic) coupling an ω-hydroxy fatty acid having the general structure (12)

with a sphingosine having the general structure (7);

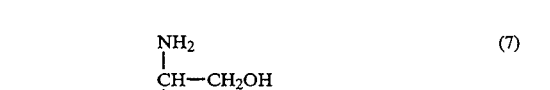

to form an intermediate having the general structure (13);

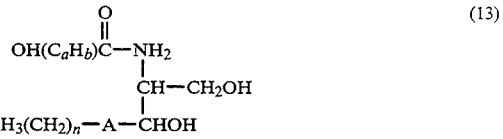

(iic) protection of the hydroxyl groups of the intermediate having the general structure (13) to give an intermediate having the general structure (14);

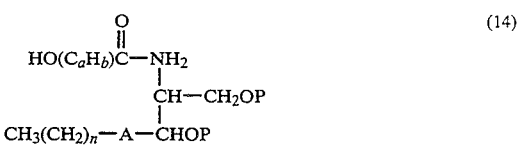

(iiic) esterification of the intermediate (14) with a $C_{14}$ to $C_{22}$ fatty acid having the general structure (4);

and
(ivc) removal of the protection groups to provide the ω-hydroxy fatty acid containing ceramide having the general structure (1); and
synthesis D comprises:
(id) coupling a long chain diol having the general structure (15);

with a $C_{14-22}$ fatty acid having the general structure (4) or on acid chloride derivative thereof;

to give an intermediate having the general structure (16);

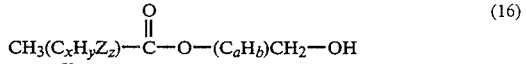

(iid) oxidation of the free hydroxyl group on intermediate (16) to give an intermediate having the general structure (6);

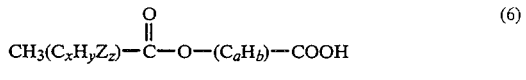

and
(iiid) coupling the intermediate (6) with sphingosine having the general structure (7);

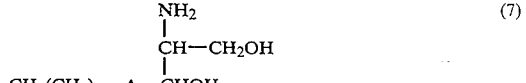

to form the ω-hydroxy fatty acid containing ceramide having the general structure (1).

2. A method of synthesising an ω-hydroxy fatty acid containing ceramide according to claim 1 wherein the protection group (P) is t-butylalcohol.

3. A method of synthesising an ω-hydroxy fatty acid containing ceramide according to claim 1 wherein the $C_{14\text{-}22}$ fatty acid having the general structure (4) is linoleic acid.

4. A method of synthesising an ω-hydroxy fatty acid containing ceramide according to claim 1 wherein, in the sphingosine molecule having the general structure (7) n is 12.

5. A method of synthesising an ω-hydroxy fatty acid containing ceramide according to claim 1 wherein in the sphingosine molecule having the general structure (7), A is the group —CH=CH—.

6. A method of synthesising an ω-hydroxy fatty acid containing ceramide according to claim 1 wherein the ceramide synthesised has the structure (17)

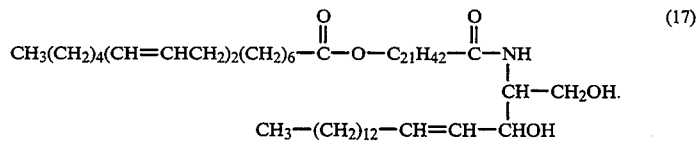

7. A method of synthesising an ω-hydroxy fatty acid containing ceramide according to claim 1, wherein the ceramide synthesised has the structure (18)

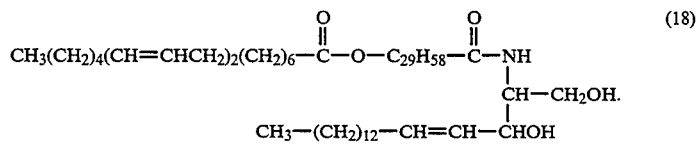

* * * * *